US005284946A

United States Patent [19]

Knüppel et al.

[11] Patent Number: 5,284,946

[45] Date of Patent: Feb. 8, 1994

[54] TRIAZINYL-SUBSTITUTED ACRYLIC ESTERS

[75] Inventors: Peter C. Knüppel, Ermelskirchen; Dieter Berg, Wuppertal; Stefan Dutzmann, Hilden; Heinz-Wilhelm Dehne, Monheim; Gerd Hänssler, Leverkusen, all of Fed. Rep. of Germany

[73] Assignee: Bayer Aktiengesellschaft, Leverkusen, Fed. Rep. of Germany

[21] Appl. No.: 29,489

[22] Filed: Mar. 11, 1993

Related U.S. Application Data

[62] Division of Ser. No. 846,321, Mar. 5, 1992, Pat. No. 5,238,934.

[30] Foreign Application Priority Data

Mar. 13, 1991 [DE] Fed. Rep. of Germany ....... 4108029

[51] Int. Cl.[5] .................. C07D 401/12; C07D 401/06; C07D 251/16; C07D 251/30

[52] U.S. Cl. .................................... 544/219; 544/197; 544/198; 544/206; 544/207; 544/208; 544/209; 544/211; 544/212

[58] Field of Search ............... 544/219, 197, 198, 206, 544/207, 208, 209, 211, 212

[56] References Cited

U.S. PATENT DOCUMENTS 4,889,882 12/1989 Nelson et al. ....................... 524/100

*Primary Examiner*—John M. Ford
*Attorney, Agent, or Firm*—Sprung Horn Kramer & Woods

[57] ABSTRACT

There are described new triazinyl-substituted acrylic esters of the formula (I)

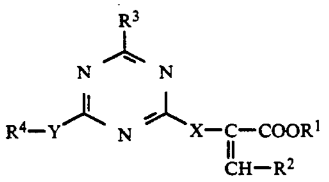

(I)

in which $R^1$, $R^2$, $R^3$, $R^4$, X and Y have the meaning given in the description, and a process for their preparation.

The new acrylic esters of the formula (I) are used for the preparation of pesticides.

1 Claim, No Drawings

TRIAZINYL-SUBSTITUTED ACRYLIC ESTERS

This is a division of application Ser. No. 07/846,321, filed Mar. 5, 1992, now U.S. Pat. No. 5,238,934.

The invention relates to new triazinyl-substituted acrylic esters, to a process for their preparation, to their use in pesticides, and to intermediates, some of which are new.

It has been disclosed that certain substituted acrylic esters such as, for example, the compound methyl 3-methoxy-2-(2-methylphenyl)acrylate, have fungicidal properties (cf. for example, EP 178 826). It has also been disclosed that certain pyrimidines such as, for example, the compound 2,4-dichloro-5-methylthiopyrimidinyl-6-thiocyanate also have fungicidal properties (cf., for example, U.S. Pat. No. 4,652,569; DE-OS (German Published Specification) 3,509,437).

It has also been disclosed that triazinyloxy(thio)acrylic acid derivatives show a herbicidal, fungicidal and plant-growth-regulatory action (compare EP-OS (European Published Specification) 409,369).

However, the activity of these previously known compounds is not entirely satisfactory in all fields of application, in particular when low amounts and concentrations are applied.

New triazinyl-substituted acrylic esters of the general formula (I) have been found

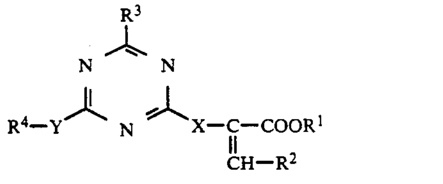

(I)

in which $R^1$ represents alkyl, $R^2$ represents dialkylamino or a radical —O—$R^5$, X represents oxygen, sulphur or a radical

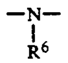

$R^3$ represents hydrogen, alkyl or alkoxy, $R^4$ represents optionally substituted aryl or heretoaralkyl, $R^5$ represents hydrogen, alkyl or optionally substituted aralkyl, $R^6$ represents hydrogen, alkyl or in each case optionally substituted aralkyl or aryl and Y represents a direct bond, oxygen or in each case one of the following groups —$CH_2$; —CH═CH— or —C≡C—.

The compounds of the formula (I) can exist as geometric isomers or mixtures of isomers of various compositions. The invention claims the pure isomers as well as the mixtures of isomers.

Furthermore, it has been found that the new triazinyl-substituted acrylic esters of the general formula (I)

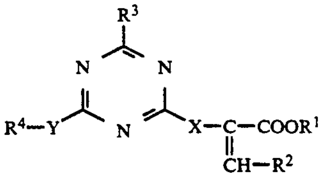

(I)

in which $R^1$ represents alkyl, $R^2$ represents dialkylamino or represents a radical —O—$R^5$, X represents oxygen, sulphur or a radical

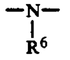

$R^3$ represents hydrogen, alkyl or alkoxy, $R^4$ represents optionally substituted aryl or heteroaryl, $R^5$ represents hydrogen, alkyl or represents optionally substituted aralkyl, $R^6$ represents hydrogen, alkyl or represents in each case optionally substituted aralkyl or aryl and p0 Y represents a direct bond, oxygen or in each case one of the following groups —$CH_2$—; —CH=CH— or —C≡C— and the isomers or mixtures of isomers thereof are obtained when substituted acetic esters of the formula (II)

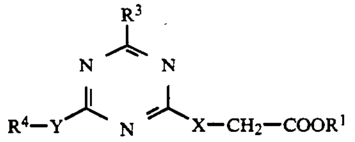

(II)

in which $R^1$, $R^2$, X, Y and $R^4$ have the abovementioned meaning, are reacted with alkoxy-bis-(dialkylamino)-methane compounds of the formula (III)

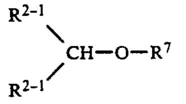

(III)

in which $R^{2-1}$ represents dialkylamino and $R^7$ represents alkyl or cycloalkyl, if appropriate in the presence of a diluent, and, if appropriate, the resulting 3-dialkylaminoacrylic acid derivatives of the formula (Ia)

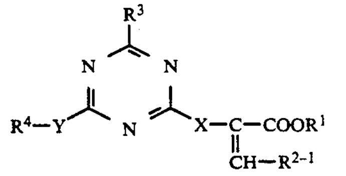

(Ia)

in which $R^1$, $R^{2-1}$, $R^3$, $R^4$, X and Y have the abovementioned meaning, are subsequently hydrolysed in a 2nd step using dilute mineral acids, and the resulting 3-hydroxyacrylic esters of the formula (IV)

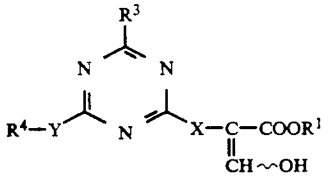

(IV)

in which $R^1R^3$, $R^4$, X and Y have the abovementioned meaning, are subsequently, in a 3rd step, reacted with alkylating agents of the formula (v)

$$R^5—E^1 \quad (V)$$

in which $E^1$ represents an electron-withdrawing leaving group and $R^5$ has the abovementioned meaning, if appropriate in the presence of a diluent and if appropriate in the presence of a reaction auxiliary.

Finally, it has been found that the new triazinyl-substituted acrylic esters of the general formula (I) have a good action against pests.

Surprisingly, the triazinyl-substituted acrylic esters of the general formula (I) according to the invention show a considerably more powerful fungicidal activity than the acrylic esters which are known from the prior art such as, for example, the compound methyl 3-methoxy-2-(2-methylphenyl)-acrylate or the compound 2,4-dichloro-5methylthlthiopyrimidinyl 6-thiocyanate, which are similar compounds chemically and from the point of view of their action.

Formula (I) provides a general definition of the triazinyl-substituted acrylic esters according to the invention. Preferred compounds of the formula (I) are those in which $R^1$ represents straight-chain or branched alkyl having 1 to 6 carbon atoms, $R^2$ represents dialkylamino having in each case 1 to 6 carbon atoms in the individual alkyl moieties, or represents a radical —O—$R^5$, X represents oxygen, sulphur or a radical

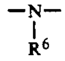

$R^3$ represents hydrogen, $C_1$–$C_6$-alkyl or $C_1$–$C_6$-alkoxy, $R^4$ represents aryl which has 6 to 10 carbon atoms or heteroaryl which has 1 to 4 identical or different hetero atoms, in particular nitrogen, oxygen and/or sulphur, these aryl or heteroaryl radicals in each case being optionally monosubstituted or polysubstituted by identical or different substituents, suitable substituents which may be mentioned being: halogen, alkyl, cycloalkyl, alkoxy, alkylthio, halogenoalkyl, halogenoalkoxy, halogenoalkylthio, dioxyalkylene, halogen-substituted dioxyalkylene, or in each case optionally substituted phenyl, phenoxy, benzyl, phenylethyl, phenylethenyl or phenylethinyl, $R^5$ represents hydrogen, straight-chain or branched alkyl having 1 to 6 carbon atoms, or represents aralkyl which has 1 to 4 carbon atoms in the straight-chain or branched alkyl moiety and 6 to 10 carbon atoms in the aryl moiety, $R^6$ represents hydrogen, straight-chain or branched alkyl having 1 to 6 carbon atoms, or represents aralkyl or aryl which has 1 to 6 carbon atoms in the straight-chain or branched alkyl moiety and 6 to 10 carbon atoms in the respective aryl moiety, and each of which is optionally monosubstituted or polysubstituted in the aryl moiety by identical or different substituents, suitable substituents in the aryl moiety in each case being the substituents mentioned in the case of $R^4$ and Y represents a direct bond, oxygen, or in each case one of the following groups —$CH_2$; —CH═CH— or —C≡C—.

Particularly preferred compounds of the formula (I) are those in which $R^1$ represents methyl, ethyl, n- or i-propyl, n-, i-, s- or t-butyl, $R^2$ represents dialkylamino having in each case 1 to 4 carbon atoms in the individual alkyl moieties, or represents a radical —O—$R^5$, X represents oxygen, sulphur or a radical

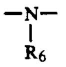

$R^3$ represents hydrogen, $C_1$–$C_4$-alkyl or $C_1$–$C_4$-alkoxy, $R^4$ represents phenyl or heteroaryl which has one or two identical or different hetero atoms, in particular nitrogen, oxygen and/or sulphur, and 4 to 6 carbon atoms, and each of which is optionally monosubstituted to trisubstituted by identical or different substituents, substituents which may be mentioned being: fluorine, chlorine, bromine, methyl, ethyl, n- or i-propyl, n-, i-, s- or t-butyl, cyclopentyl, cyclohexyl, methoxy, ethoxy, n- or i-propoxy, methylthio, ethylthio, trifluoromethyl, trifluoromethoxy, trifluoromethylthio, dioxymethylene, dioxyethylene, tetrafluorodioxyethylene, difluorodioxymethylene, or phenyl, phenoxy, benzyl, phenylethyl, phenylethenyl or phenylethinyl, each of which is optionally monosubstituted to trisubstituted by identical or different substituents from the series comprising fluorine, chlorine, methyl, methoxy or trifluoromethyl, $R^5$ represents hydrogen, methyl, ethyl, n- or i-propyl, n-, i-, s- or t-butyl, or represents benzyl, and $R^6$ represents hydrogen, methyl, ethyl, n- or i-propyl, n-, i-, s- or t-butyl, or represents benzyl or phenyl, and Y represents a direct bond, oxygen, or in each case one of the following groups —$CH_2$—; —CH═CH— or —C≡C—.

Very particularly preferred compounds of the formula (I) are those in which $R^1$ represents methyl or ethyl, $R^2$ represents dimethylamino, hydroxyl, methoxy or ethoxy, X represents a radical

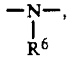

$R^3$ represents hydrogen, $C_1$–$C_4$-alkyl or $C_1$–$C_4$-alkoxy, $R^4$ represents phenyl or pyridyl, each of which is optionally monosubstituted to trisubstituted by identical or different substituents, suitable substituents which may be mentioned being: fluorine, chlorine, bromine, methyl, ethyl, t-butyl, cyclohexyl, methoxy, ethoxy, trifluoromethyl, trifluoromethoxy, dioxymethylene, difluorodioxymethylene, dioxyethylene, tetrafluorodioxyethylene or phenyl, phenoxy or phenylethinyl, each of which is optionally monosubstituted to trisubstituted by identical or different substituents from the series comprising fluorine, chlorine, methyl, methoxy or trifluoromethyl, $R^6$ represents hydrogen, methyl, ethyl or benzyl and Y represents a direct bond, oxygen, or in each case one of the following groups $-CH_2$; $-CH{=}CH-$ or $-C{\equiv}C-$.

The definitions of the radicals mentioned here analogously also apply to the starting materials and intermediates.

Moreover, the abovementioned combinations represent preferred combinations of the individual radicals. However, the individual definitions of the radicals can also be exchanged as desired from amongst each other, that is to say also between the respective preferred ranges of the combinations mentioned.

Aryl as such or in compositions preferably represents phenyl or naphthyl, in particular phenyl.

All aliphatic radicals as such or in compositions are straight-chain or branched and contain preferably 1 to 6, in particular 1 to 4, very especially 1 or 2, carbon atoms.

Unless otherwise defined, halogen preferably represents fluorine, chlorine, bromine or iodine, in particular fluorine, chlorine or bromine.

The following triazinyl-substituted acrylic esters of the general formula (I) may be mentioned individually in addition to the compounds mentioned in the preparation examples:

TABLE 1

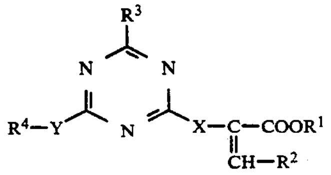

(I)

| $R^1$ | $R^2$ | $R^3$ | $R^4$ | X | Y |
|---|---|---|---|---|---|
| $CH_3$ | $OCH_3$ | H | 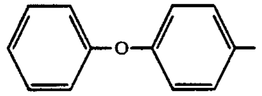 | $-N(CH_3)-$ | bond |
| $CH_3$ | $OCH_3$ | H | 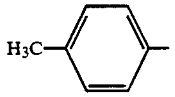 | $-N(CH_3)-$ | bond |
| $CH_3$ | $OCH_3$ | H | 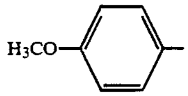 | $-N(CH_3)-$ | bond |
| $CH_3$ | $OCH_3$ | H | 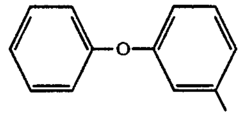 | $-N(CH_3)-$ | bond |
| $CH_3$ | $OCH_3$ | H | 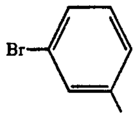 | $-N(CH_3)-$ | bond |
| $CH_3$ | $OCH_3$ | H | 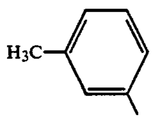 | $-N(CH_3)-$ | bond |
| $CH_3$ | $OCH_3$ | H | 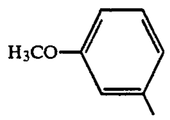 | $-N(CH_3)-$ | bond |

TABLE 1-continued
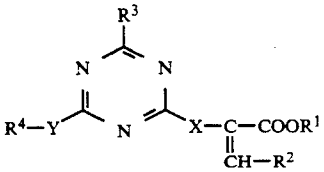
(I)
| $R^1$ | $R^2$ | $R^3$ | $R^4$ | X | Y |
|---|---|---|---|---|---|
| $CH_3$ | $OCH_3$ | H | 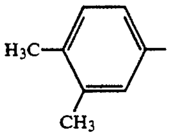 | $-N(CH_3)-$ | bond |
| $CH_3$ | $OCH_3$ | H | 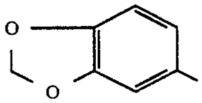 | $-N(CH_3)-$ | bond |
| $CH_3$ | $OCH_3$ | H | 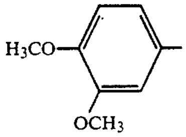 | $-N(CH_3)-$ | bond |
| $CH_3$ | $OCH_3$ | H | 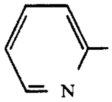 | $-N(CH_3)-$ | bond |
| $CH_3$ | $OCH_3$ | H | 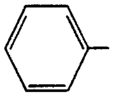 | $-N(CH_3)-$ | $-C \equiv C-$ |
| $CH_3$ | $OCH_3$ | H | 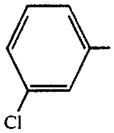 | $-N(CH_3)-$ | $-C \equiv C-$ |
| $CH_3$ | $OCH_3$ | H | 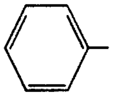 | $-N(CH_3)-$ | O |
| $CH_3$ | $OCH_3$ | H | 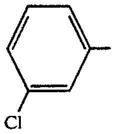 | $-N(CH_3)-$ | O |
| $CH_3$ | $OCH_3$ | H | 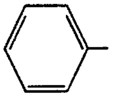 | $-N(CH_3)-$ | $-CH_2-$ |
| $CH_3$ | $OCH_3$ | H | 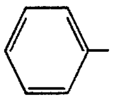 | $-N(CH_3)-$ | $-CH=CH-$ |

TABLE 1-continued

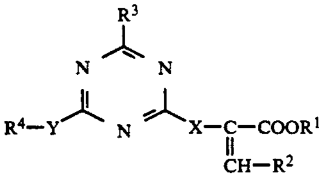

(I)

| R1 | R2 | R3 | R4 | X | Y |
|---|---|---|---|---|---|
| $CH_3$ | $OCH_3$ | H | 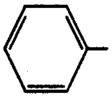 | O | bond |
| $CH_3$ | $OCH_3$ | H | 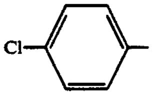 | O | bond |
| $CH_3$ | $OCH_3$ | H | 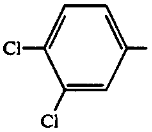 | O | bond |
| $CH_3$ | $OCH_3$ | H | 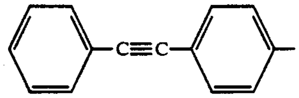 | 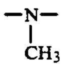 | bond |
| $CH_3$ | $OCH_3$ | H | 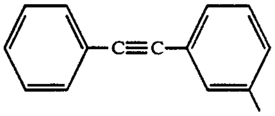 | 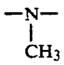 | bond |
| $CH_3$ | $OCH_3$ | H | 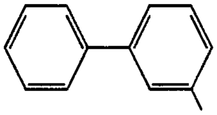 | 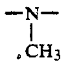 | bond |
| $CH_3$ | $OCH_3$ | H | 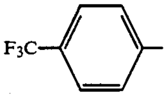 | 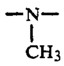 | bond |

If, for example, methyl N-[2-(4-phenyl)-triazinyl]-N-methylaminoacetate and t-butoxy-bis(dimethylamino)methane as well as dimenthyl sulphate are used as starting substances, the course of the reaction of the process according to the invention can be represented by the following equation:

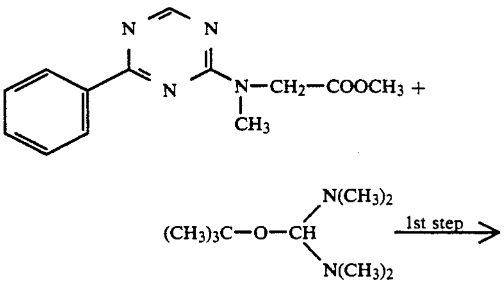

-continued

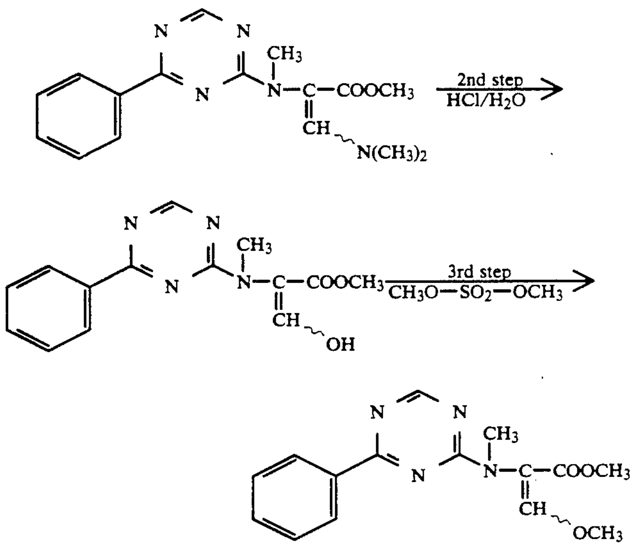

The substituted acetic esters of the formula (II) are new and the subject of the invention. They can be prepared analogously to methods known from the literature, by reacting halogen-substituted 1,3,5-triazine derivatives of the formula (V)

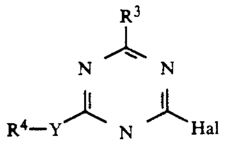

(V)

in which $R^3$, $R^4$ and Y have the abovementioned meaning and

Hal represents halogen, in particular chlorine, with sarcosic esters of the formula (VI)

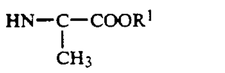

(VI)

in which $R^1$ has the abovementioned meaning, if appropriate in the presence of a base (compare, for example, DE-OS (German Published Specification) 3,904,931 and Preparation Examples.

The compounds of the formula (V) are known (compare, for example, WO 810 30 20; Aust. J. Chem., 34, 623 (1981); Synthesis 1980, 841).

The compounds of the formula (VI) are generally known compounds of organic chemistry.

Formula (III) provides a general definition of the alkoxy-bis-(dialkylamino)-methane compounds furthermore required as starting substances for carrying out the process according to the invention. In this formula (III), $R^{2-1}$ preferably represents dialkylamino having in each case 1 to 6 carbon atoms, particularly preferably 1 to 4 carbon atoms, in the individual straight-chain or branched alkyl moieties.

$R^7$ preferably represents secondary or tertiary alkyl having 3 to 8 carbon atoms or represents cycloalkyl having 5 to 7 carbon atoms, in particular t-butyl or cyclohexyl.

The alkoxy-bis(dialkylamino)-methane derivatives of the formula (III) are known (cf., for example, Chem. Ber. 101, 41-50 [1968]; Chem. Ber. 101, 1885-1888 [1968]; DE 2,303,919; PCT Int. Appl. WO 860 12 04) or can be obtained analogously to known processes. The intermediates of the formula (IV) are new and also a subject of the invention.

Formula (V) provides a general definition of the alkylating agents furthermore required as starting substances for carrying out the 3rd step of the process according to the invention. In this formula (V), $R^5$ preferably represents those radicals which have already been mentioned in connection with the description of the substances of the formula (I) according to the invention as being preferred for this substituent.

$E^1$ represents a leaving group customary in the case of alkylating agents, preferably an optionally substituted alkyl, alkoxy or arylsulphonyloxy radical, such as, for example, a methoxysulphonyloxy radical, an ethoxysulphonyloxy radical or a p-toluene sulphonyloxy radical, or represents halogen, in particular chlorine, bromine or iodine.

The alkylating agents of the formula (V) are generally known compounds of organic chemistry.

Suitable diluents for carrying out the 1st step of the process according to the invention are inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform, carbon tetrachloride, ethers such as diethyl ether, dioxane, tetrahydrofuran or ethylene glycol dimethyl ether or ethylene glycol diethyl ether, amides such as dimethylformamide, dimethylacetamide, N-methylformanilide , N-methylpyrrolidone or hexamethylphosphoric triamide.

The 1st step of the process according to the invention is preferably to be carried out without any addition of solvents.

When carrying out the 1st step of the process according to the invention, the reaction temperatures can be varied within a substantial range. In general, it is carried out at temperatures between −35° C. and +150° C., preferably at temperatures between 0° C. and 120° C.

The 1st step of the process according to the invention can also be carried out under reduced or increased pressure, but preferably under atmospheric pressure.

If appropriate, it may be expedient to use an inert gas atmosphere such as, for example, nitrogen or argon, but in general it is possible to carry out the 1st step of the process according to the invention under a standard ambient atmosphere.

For carrying out the 1st step of the process according to the invention, 1.0 to 15.0 moles, preferably 1.0 to 12.0 moles, of alkoxy-bis-(dialkylamino)-methane compound of the formula (III) are generally employed per mole of substituted acetic ester of the formula (II).

The reaction is carried out and the reaction products are worked up and isolated by generally customary methods (cf. also the Preparation Examples).

Acids which are suitable for carrying out the hydrolysis in the 2nd step of the process according to the invention are customary inorganic and organic acids. Aqueous solutions of inorganic mineral acids such as hydrochloric acid, sulphuric acid, phosphoric acid or nitric acid are preferably used, in particular aqueous hydrochloric acid.

Diluents which are suitable for carrying out the 2nd and 3rd step of the process according to the invention are also inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform, carbon tetrachloride, ethers such as diethyl ether, dioxane, tetrahydrofuran or ethylene glycol dimethyl ether or ethylene glycol diethyl ether, ketones such as acetone or butanone, nitriles such as acetonitrile or propionitrile, amides such as dimethylformamide, dimethylacetamide, N-methylformanilide, N-methylpyrrolidone or hexamethylphosphoric triamide, esters such as ethyl acetate, or sulphoxides such as dimethyl sulphoxide.

The 2nd step of the process according to the invention is carried out in particular in polar diluents such as acetonitrile, acetone or dimethylformamide, if appropriate also in the presence of water. If appropriate, the 3rd step of the process according to the invention can also be carried out in a two-phase system such as, for example, water/toluene or water/dichloromethane, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}/C_{15}$-alkylammonium chloride, dibenzyl-dimethyl-ammonium methylsulphate, dimethyl-$C_{12}/C_{14}$-alkyl-benzylammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

The 3rd step of the process according to the invention is preferably carried out in the presence of a suitable reaction auxiliary. Suitable reaction auxiliaries are all inorganic and organic bases which can customarily be used. The following are preferably used: the hydrides, hydroxides, amides, alcoholates, carbonates or hydrogen carbonates of alkali metals, such as, for example, sodium hydride, sodium amide, sodium hydroxide, sodium methylate, sodium ethylate, potassium t-butylate, sodium carbonate or sodium hydrogen carbonate, and also tertiary amines such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out the 2nd and 3rd step of the process according to the invention, the reaction temperatures can be varied within a substantial range. In general, they are carried out at temperatures between −30° C. and +150° C., preferably at temperatures between −20° C. and +120° C.

Both the 2nd step of the process according to the invention and the 3rd step of the process according to the invention are generally carried out under atmospheric pressure. However, it is also possible to carry out these steps under reduced or increased pressure.

For carrying out the 2nd step of the process according to the invention, 1.0 to 3.0 moles, preferably 1.0 to 2.0 moles, of dilute mineral acid are generally employed per mole of 3-dialkylaminoacrylic ester of the formula (Ia). The reaction is carried out and the reaction products are worked up and isolated by generally customary methods.

For carrying out the 3rd step of the process according to the invention, 1.0 to 5.0 moles, preferably 1.0 to 3.0 moles, of alkylating agent of the formula (V) and if appropriate 1.0 to 5.0 moles, preferably 1.0 to 3.0 moles, of reaction auxiliary are generally employed per mole of 3-hydroxyacrylic ester of the formula (IV). The reaction is carried out and the reaction products are worked up and isolated by generally customary methods.

In a particularly preferred variant, the 2nd and 3rd reaction step of the process according to the invention are carried out directly in one reaction step in a so-called "one-pot reaction" and without isolating the intermediates of the formula (IV). In this variant too, the reaction is carried out and the reaction products are worked up and isolated by generally customary methods (cf. also the Preparation Examples).

The active compounds according to the invention have a powerful action against pests and can be employed in practice for combating undesired harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some pathogens of fungal diseases which come under the generic names listed above may be mentioned as examples, but not by way of limitation:

Pythium species, such as, for example, *Pythium ultimum;* Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechlera, syn: Helminthosporium);

Cochliobolus species, such as, for example, *Cochiobolus sativus* (conidia form: Drechslera, syn: Helminthosporium)

Uromyces species, such as, for example *Uromyces appendiculatus;*

Puccinia species, such as, for example, *Puccinia recondita;*

Tilletia species, such as, for example, *Tilletia caries;*

Usilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Bjotrytis cinerea;*

Septoria species, such as, for example, septoria nodorum;

Leptosphaeria species, such as, for example, *Leptosphaeria nordorum;*

Cercospora species, such as, for example, *Cercospora canescens;*

Alternaria species, such as, for example, *Alternaria brassicac* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success protectively for combating cereal diseases such as, for example, against the pathogen causing powdery cereal mildew on barley (*Erysiphe graminis*) or against the pathogen causing leaf spot on barley (*Cochliobolus sativus*) or against the pathogen causing apple scab (*Venturia inaequalis*) or for combating rice diseases such as, for example, against the pathogen causing rice blast disease (*Pyricularia oryzae*). Mention must also be made of the good in-vitro activity of the active compounds according to the invention. The intermediates of the formulae (II) and (IV) also have fungicidal activity.

The compounds according to the invention also have a good fungicidal action against *Leptosphaeria nodorum,* mildew on wheat, *Pyrenophora teres* and *Fusarium nivale,* in particular on cereals, against Phytophthora, and a foliar-insecticidal secondary effect.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seeds, and ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilisers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound preparation or the active compound itself into the soil.

The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

In the treatment of soil, active compound concentrations of 0.00001 to 0.1% by weight, preferably 0.0001 to 0.02% by weight, are required at the place of action.

The examples which follow describe the preparation and use of the active compounds according to the invention without imposing any limitation thereto.

PREPARATION EXAMPLES

Example 1

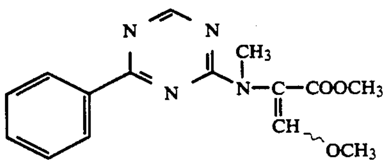

3.5 g (0.011 mol} of methyl 2-{N-[4-phenyl-1,3,5-triazin- 2-yl]-N-methylamino}-3-dimethylaminoacrylate in 350 ml of acetone there are first added 350 ml of water and then 11.2 ml (0.022 mol) of 2-normal hydrochloric acid, and the mixture is subsequently stirred for 8 hours at room temperature. After this, acetone is distilled off, and the aqueous solution is rendered neutral and extracted with ethyl acetate. The organic phase is concentrated, the residue is taken up in 100 ml of dimethylformamide, and the mixture is treated with 2.5 g (0.021 mol) of potassium carbonate and 3.2 g (0.026 mol) of dimethyl sulphate and stirred for 16 hours at room temperature. For working up, the mixture is concentrated in vacuo, and the residue is partitioned between ethyl acelale and waler. The or9anic phase is concentrated and the residue chromatographed on silica 9el (eluent: ethyl acetate).

2.8 g (83% of theory) of methyl 2-{N-[4-phenyl-1,3,5-triazin-2-yl]-N-methylamino}-3-methoxy-acrylate of melting point 98°-101° C. are obtained.

Example 2

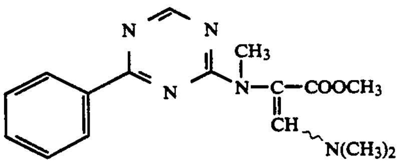

50.0 g (0.286 mol) of t-butyloxy-bis-(dimethylamino)methane are added to 6.6 g (0.025 mol) of methyl N-[4-phenyl-2-1,3,5-triazinyl]-N-methylglycinate. The reaction mixture is stirred for 16 hours at 80° C. and then poured into water and extracted with ethyl acetate. The combined, dried ethyl acetate phases are concentrated.

6,5 g (83% of theory) of methyl 2-{N-[4-phenyl-1,3,5-triazin-2-yl]-N-methylamnio}-3-dimenthylaminoacrylate are obtained as a pale brown oil.

The end products of the formula (I)

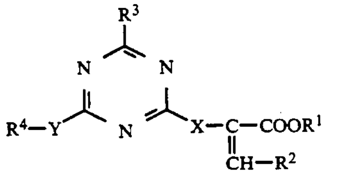

(I)

which are subsequently listed in Table 2 are obtained analogously to Example 1 and 2 and taking into consideration the instructions in the description of the process according to the invention:

TABLE 2

| Example No. | $R^1$ | $R^2$ | $R^3$ | X | Y | $R^4$ | Physical constants |
|---|---|---|---|---|---|---|---|
| 3 | $CH_3$ | $OCH_3$ | H | —N—<br>\|<br>$CH_3$ | direct bond | Cl 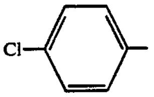 | m.p.: 114° C.-115° C. |
| 4 | $CH_3$ | $N(CH_3)_2$ | H | —N—<br>\|<br>$CH_3$ | direct bond | Cl 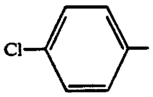 | $^1H$ NMR*: (δ = 2.95; 3.37; 3.67) |
| 5 | $CH_3$ | $OCH_3$ | H | —N—<br>\|<br>$CH_3$ | direct bond | 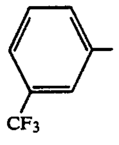 | $^1H$ NMR*: (δ = 3.42; 3.75; 3.92) |
| 6 | $CH_3$ | $N(CH_3)_2$ | H | —N—<br>\|<br>$CH_3$ | direct bond | 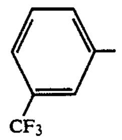 | $^1H$ NMR*: (δ = 2.97; 3.40; 3.67) |

TABLE 2-continued

| Example No. | $R^1$ | $R^2$ | $R^3$ | X | Y | $R^4$ | Physical constants |
|---|---|---|---|---|---|---|---|
| 7 | $CH_3$ | $OCH_3$ | H | $-N(CH_3)-$ | direct bond | 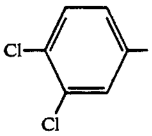 | $^1H$ NMR*: ($\delta$ = 3.42; 3.76; 3.91) |
| 8 | $CH_3$ | $N(CH_3)_2$ | H | $-N(CH_3)-$ | direct bond | 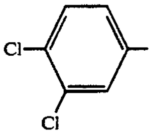 | $^1H$ NMR*: ($\delta$ = 2.96; 3.37; 3.67) |
| 9 | $CH_3$ | $OCH_3$ | H | $-N(CH_3)-$ | direct bond | 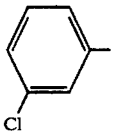 | $^1H$ NMR*: ($\delta$ = 3.39; 3.72; 3.92) |
| 10 | $CH_3$ | $N(CH_3)_2$ | H | $-N(CH_3)-$ | direct bond | 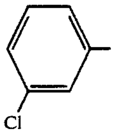 | $^1H$ NMR*: ($\delta$ = 2.95; 3.38; 3.67) |
| 11 | $CH_3$ | $OCH_3$ | H | $-N(CH_3)-$ | direct bond | 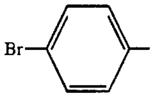 | m.p.: 140° C.-142° C. |
| 12 | $CH_3$ | $N(CH_3)_2$ | H | $-N(CH_3)-$ | direct bond | 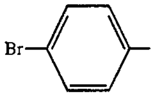 | $^1H$ NMR*: ($\delta$ = 2.95; 3.37; 3.67) |
| 13 | $CH_3$ | $OCH_3$ | H | $-N(CH_3)-$ | direct bond | 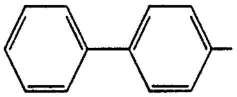 | m.p.: 154° C.-157° C. |
| 14 | $CH_3$ | $N(CH_3)_2$ | H | $-N(CH_3)-$ | direct bond | 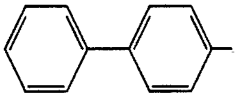 | $^1H$ NMR*: ($\delta$ = 2.97; 3.40; 3.68) |
| 15 | $CH_3$ | $OCH_3$ | H | $-N(CH_3)-$ | direct bond | 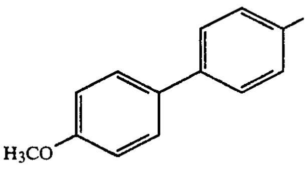 | m.p.: 137° C.-138° C. |
| 16 | $CH_3$ | $N(CH_3)_2$ | H | $-N(CH_3)-$ | direct bond | 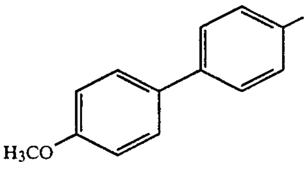 | m.p.: 137° C.-139° C. |
| 17 | $CH_3$ | $N(CH_3)_2$ | H | $-N(CH_3)-$ | direct bond | 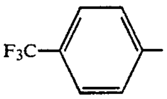 | $^1H$-NMR*: ($\delta$ = 2,95; 3,40; 3,68) |

TABLE 2-continued

| Example No. | $R^1$ | $R^2$ | $R^3$ | X | Y | $R^4$ | Physical constants |
|---|---|---|---|---|---|---|---|
| 18 | $CH_3$ | $OCH_3$ | H | $-N-$<br>$CH_3$ | direct bond | 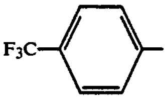 | m.p.: 93° C. |
| 19 | $CH_3$ | $N(CH_3)_3$ | H | $-N-$<br>$CH_3$ | direct bond | 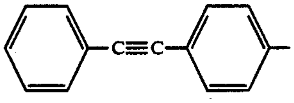 | $^1$H-NMR*: ($\delta$ = 2,96; 3,39; 3,67) |
| 20 | $CH_3$ | $OCH_3$ | H | $-N-$<br>$CH_3$ | direct bond | 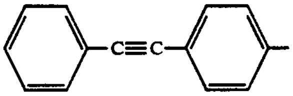 | $^1$H-NMR*: ($\delta$ = 3,37; 3,75; 3,91) |
| 21 | $CH_3$ | $N(CH_3)_2$ | H | $-N-$<br>$CH_3$ | direct bond | 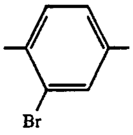 | $^1$H-NMR*: ($\delta$ = 2,94; 3,48; 3,62) |
| 22 | $CH_3$ | $OCH_3$ | H | $-N-$<br>$CH_3$ | direct bond | 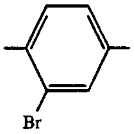 | $^1$H-NMR*: ($\delta$ = 3,37; 3,74; 3,92) |
| 23 | $CH_3$ | $N(CH_3)_2$ | H | $-N-$<br>$CH_3$ | direct bond | 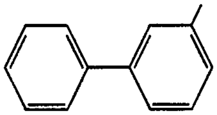 | $^1$H-NMR*: ($\delta$ = 2,94; 3,40; 3,67) |
| 24 | $CH_3$ | $N(CH_3)_3$ | H | $-N-$<br>$CH_3$ | direct bond | 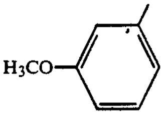 | $^1$H-NMR*: ($\delta$ = 2,92; 3,36; 3,90) |
| 25 | $CH_3$ | $N(CH_3)_2$ | H | $-N-$<br>$CH_3$ | direct bond | 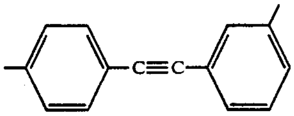 | $^1$H-NMR*: ($\delta$ = 2,92; 3,40; 3,67) |
| 26 | $CH_3$ | $OCH_3$ | H | $-N-$<br>$CH_3$ | direct bond | 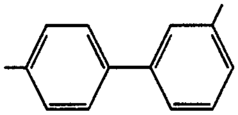 | $^1$H-NMR*: ($\delta$ = 3,40; 3,73; 3,91) |
| 27 | $CH_3$ | $OCH_3$ | H | $-N-$<br>$CH_3$ | direct bond | 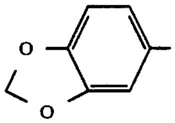 | $^1$H-NMR*: ($\delta$ = 2,91; 3,35; 3,91) |
| 28 | $CH_3$ | $N(CH_3)_2$ | H | $-N-$<br>$CH_3$ | direct bond | 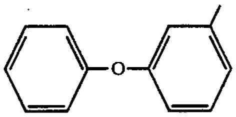 | $^1$H-NMR*: ($\delta$ = 2,87; 3,33; 3,64) |

TABLE 2-continued

| Example No. | $R^1$ | $R^2$ | $R^3$ | X | Y | $R^4$ | Physical constants |
|---|---|---|---|---|---|---|---|
| 29 | $CH_3$ | $OCH_3$ | H | $-N(CH_3)-$ | direct bond | 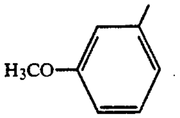 | $^1$H-NMR*: ($\delta$ = 3,37; 3,72; 3,90) |
| 30 | $CH_3$ | $OCH_3$ | H | $-N(CH_3)-$ | direct bond | 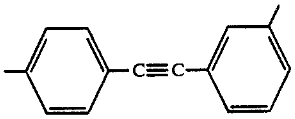 | $^1$H-NMR*: ($\delta$ = 2,90; 3,58; 3,91) |
| 31 | $CH_3$ | $OCH_3$ | H | $-N(CH_3)-$ | direct bond | 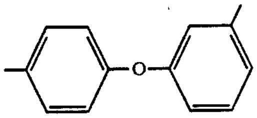 | $^1$H-NMR*: ($\delta$ = 3,32; 3,69; 3,87) |
| 32 | $CH_3$ | $OCH_3$ | H | $-N(CH_3)-$ | O | 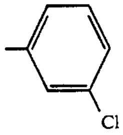 | |
| 33 | $CH_3$ | $OCH_3$ | H | $-N(CH_3)-$ | O | 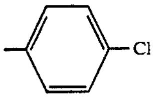 | |
| 34 | $CH_3$ | $OCH_3$ | H | $-N(CH_3)-$ | O | 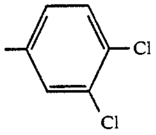 | |
| 35 | $CH_3$ | $OCH_3$ | H | $-N(CH_3)-$ | O | 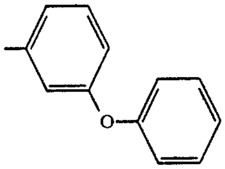 | |
| 36 | $CH_3$ | $OCH_3$ | H | $-N(CH_3)-$ | O | 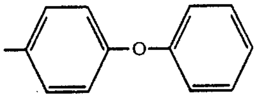 | |
| 37 | $CH_3$ | $OCH_3$ | H | $-N(CH_3)-$ | O | 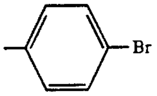 | |
| 38 | $CH_3$ | $OCH_3$ | H | $-N(CH_3)-$ | O | 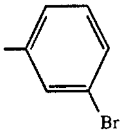 | |
| 39 | $CH_3$ | $OCH_3$ | H | $-N(CH_3)-$ | O | 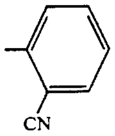 | |

TABLE 2-continued

| Example No. | $R^1$ | $R^2$ | $R^3$ | X | Y | $R^4$ | Physical constants |
|---|---|---|---|---|---|---|---|
| 40 | $CH_3$ | $OCH_3$ | H | $-N(CH_3)-$ | O | 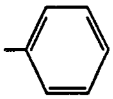 | |
| 41 | $CH_3$ | $OCH_3$ | Cl | $-N(CH_3)-$ | O | 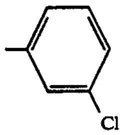 | |
| 42 | $CH_3$ | $OCH_3$ | Cl | $-N(CH_3)-$ | O | 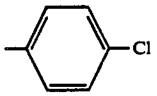 | |
| 43 | $CH_3$ | $OCH_3$ | Cl | $-N(CH_3)-$ | O | 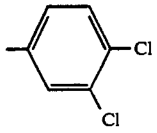 | |
| 44 | $CH_3$ | $OCH_3$ | Cl | $-N(CH_3)-$ | O | 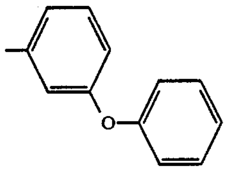 | |
| 45 | $CH_3$ | $OCH_3$ | Cl | $-N(CH_3)-$ | O | 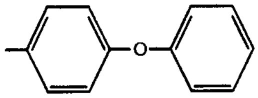 | |
| 46 | $CH_3$ | $OCH_3$ | Cl | $-N(CH_3)-$ | O | 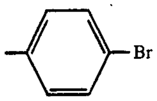 | |
| 47 | $CH_3$ | $OCH_3$ | Cl | $-N(CH_3)-$ | O | 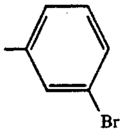 | |
| 48 | $CH_3$ | $OCH_3$ | Cl | $-N(CH_3)-$ | O | 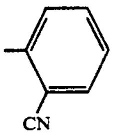 | |
| 49 | $CH_3$ | $OCH_3$ | Cl | $-N(CH_3)-$ | O | 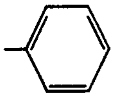 | |

*The $^1H$ NMR spectra are recorded in deuterochloroform ($CDCl_3$) with tetramethylsilane (TMS) as the internal standard. The figures indicate the chemical shift of the methyl groups ($N(\underline{CH_3})_2$, $O\underline{CH_3}$, $>N-\underline{CH_3}$ and $-COO\underline{CH_3}$) as δ value in ppm.

Preparation of the Starting Compound

Example II-1

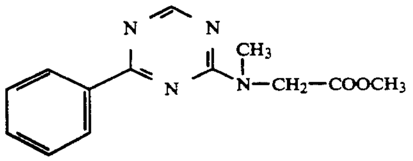

25.5 g (0.183 mol) of methyl sarcosinate hydrochloride and 27.7 g (0.274 mol) of triethylamine are added to 17.5 g (0.092 mol) of 2-chloro-4-phenyl-1,3,5-triazine in 200 ml of dioxane, and this reaction mixture is stirred at room temperature for 16 hours. For working up, the mixture is treated with water and extracted with ethyl acetate. The combined, dried ethyl acetate phases are concentrated in vacuo, and the residue is chromatographed on silica gel (eluent: ethyl acetate, hexane 1:3).

13.7 g (58% of theory) of methyl N-[(phenyl-2-1,3,5-triazinyl)-N-methyl]-glycinate of melting point 71°–73° C. are obtained.

USE EXAMPLES

In the Use Examples which follow, the compounds listed below are applied as comparison substances:

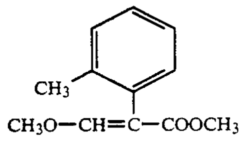

Methyl 3-methoxy-2-(2-methylphenyl)-acrylate (disclosed in EP 178,826)

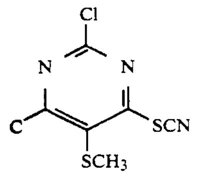

2,4-Dichloro-5-methylthiopyrimidinyl 6-thiocyanate (disclosed in US Patent Specification 4,652,569).

Example A

Erysiphe Test (Barley)/Protective

Solvent: 100 parts by weight of dimethylformamide
Emulsifier: 0.25 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation until dew-moist. After the spray coating has dried on, the plants are dusted with spores of *Erysiphe graminis* f.sp.hordei.

The plants are placed in a greenhouse at a temperature of approx. 20° C. and a relative atmospheric humidity of approx. 80% to enhance the development of mildew pustules.

The test is evaluated 7 days after inoculation.

An activity of more than 50 degrees of effectiveness above the prior art is shown in this test, for example, by the compounds of the following Preparation Examples: 1 and 5.

Example B

*Cochliobolus sativus* Test (Barley)/Protective

Solvent: 100 parts by weight of dimethylformamide
Emulsifier: 0.25 parts by weight of alkylaryl polyglycol ether To prepare a suitable preparation of active compound, part by weight of active compound is mixed with the stated amounts of solvent and emulsifier, and the concentrate is diluted with water to the desired concentration.

To test for protective activity, young plants are sprayed with the active compound preparation until dew-moist. After the spray coating has dried on, the plants are sprayed with a conidia suspension of *Cochliobolus sativus.* The plants remain in an incubation cabin for 48 hours at 20° C. and 100% relative atmospheric humidity.

The plants are placed in a greenhouse at a temperature of approx. 20° C. and a relative atmospheric humidity of approx. 80%.

The test is evaluated 7 days after inoculation.

In this test, a clearly superior activity compared with the prior art is shown, for example, by the compound of Preparation Example 3.

Example C

Venturia Test (Apple)/Protective

Solvent: 4.7 parts by weight of acetone
Emulsifier: 0.3 part by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation until dripping wet. After the spray coating has dried on, the plants are inoculated with an aqueous conidia suspension of the pathogen causing apple scab (*Venturia inaequalis*) and then remain for 1 day in an incubation cabin at 20° C. and 100% relative atmospheric humidity.

The plants are then placed in a greenhouse at 20° C. under a relative atmospheric humidity of approx. 70%.

The test is evaluated 12 days after inoculation.

In this test, a clearly superior activity compared with the prior art is shown, for example, by the compounds of the following Preparation Examples: 1, 7, 9, 11 and 13.

Example D

Pyricularia Test (Rice)/Protective

Solvent 12.5 parts by weight of acetone
Emulsifier: 0.3 parts by weight of alkylaryl polyglycol ether To prepare a suitable preparation of active compound, 1 part by weight of active compound is mixed with the stated amount of solvent and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are subsequently placed in a greenhouse at 100% relative atmospheric humidity and 25° C.

The level of disease is evaluated 4 days after inoculation.

In this test, a clearly superior activity compared with the prior art is shown, for example, by the compounds of the following Preparation Examples: 1, 3 and 5.

We claim:

1. Acetic esters of the Formula II (II)

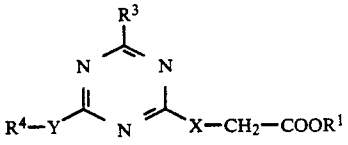

in which $R^1$ represents straight-chain or branched alkyl having 1 to 6 carbon atoms, X represents oxygen, sulphur, or a radical

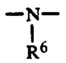

$R^3$ represents hydrogen, $C_1$-$C_6$-alkyl, or $C_1$-$C_6$-alkoxy, $R^4$ represents aryl which has 6 to 10 carbon atoms or pyridyl, each of which is optionally monosubsituted or polysubstituted by identical or different substituents selected from the group consisting of fluorine, chlorine, bromine, methyl, ethyl, n- or i-propyl, n-, i-, s- or t-butyl, cyclopentyl, cyclohexyl, methoxy, ethoxy, n- or i-propoxy methylthio, ethylthio, trifluoromethyl, trifluoromethyoxy, trifluoromethylthio, doixymethylene, dioxyethylene, tetrafluorodioxymethylene, difluorodioxymethylene, or phenyl, phenoxy, benzyl, phenylethyl, phenylethenyl, or phenylethinyl, each of which is optionally monosubsituted to trisubstituted by identical or different substituents selected from the group consisting of fluorine, chlorine, methyl, methoxy, or trifluoromethyl, $R^6$ represents hydrogen, straight-chain or branched alkyl having 1 to 6 carbon atoms, or represents aralkyl or aryl which has 1 to 6 carbon atoms in the straight-chain or branched-alkyl moiety and 6 to 10 carbon atoms in the respective aryl moiety, and each of which is optionally monosubstituted or polysubstituted in the aryl moiety by identical or different substituents selected from the group consisting of the substituents mentioned in the case of $R^4$, and Y represents a direct bond, oxygen, or in each case one of the following groups $—CH_2$, —CH—CH, or C≡C.

* * * * *

UNITED STATES PATENT AND TRADEMARK OFFICE

CERTIFICATE OF CORRECTION

PATENT NO. : 5,284,946

DATED : February 8, 1994

INVENTOR(S) : Peter C. Knuppel, et al.

It is certified that error appears in the above-indentified patent and that said Letters Patent is hereby corrected as shown below:

| | |
|---|---|
| Column 30, line 14, | after "i-propoxy" insert a "," (comma) |
| Column 30, lines 15 and 16, | cancel "trifluoromethyoxy" and substitute --trifluoromethoxy-- |

Signed and Sealed this

Nineteenth Day of January, 1999

Attest:

Attesting Officer

*Acting Commissioner of Patents and Trademarks*